US00PP23063P2

(12) United States Plant Patent
Retkes

(10) Patent No.: US PP23,063 P2
(45) Date of Patent: Sep. 18, 2012

(54) ***OXALIS* PLANT NAMED 'JROXACHVEL'**

(50) Latin Name: *Oxalis regnellii*
Varietal Denomination: Jroxachvel

(76) Inventor: József Retkes, Szombathely (HU)

( * ) Notice: Subject to any disclaimer, the term of this patent is extended or adjusted under 35 U.S.C. 154(b) by 68 days.

(21) Appl. No.: 12/930,164

(22) Filed: Dec. 29, 2010

(51) Int. Cl.
*A01H 5/00* (2006.01)

(52) U.S. Cl. ..... Plt./463
(58) Field of Classification Search ..... Plt./463
See application file for complete search history.

*Primary Examiner* — June Hwu
(74) *Attorney, Agent, or Firm* — C. A. Whealy

(57) ABSTRACT

A new and distinct cultivar of *Oxalis* plant named 'Jroxachvel', characterized by its upright, outwardly spreading and uniformly mounded plant habit; numerous basal leaves; dense and bushy plant form; freely flowering habit; dark brown-colored leaves; white-colored flowers; and relative tolerance to high light levels.

1 Drawing Sheet

Botanical designation: *Oxalis regnellii*.
Cultivar denomination: 'JROXACHVEL'.

BACKGROUND OF THE INVENTION

The present invention relates to a new and distinct cultivar of *Oxalis* plant, botanically known as *Oxalis regnellii* and hereinafter referred to by the name 'Jroxachvel'.

The new *Oxalis* plant is a product of a planned breeding program conducted by the Inventor in Szombathely, Hungary. The objective of the breeding program is to create new freely-flowering *Oxalis* plants that have an improved propagation rate and tolerance to high light levels.

The new *Oxalis* plant originated from a cross-pollination made by the Inventor in Szombathely, Hungary during the summer of 2003 of a proprietary selection of *Oxalis regnellii* identified as code number M6, not patented, as the female, or seed parent with a proprietary selection of *Oxalis regnellii* identified as code number L7, not patented, as the male, or pollen, parent. The new *Oxalis* plant was discovered and selected by the Inventor as a single flowering plant from within the progeny of the stated cross-pollination in a controlled greenhouse environment in Szombathely, Hungary in 2005.

Asexual reproduction of the new *Oxalis* plant by tissue culture in Gensingen, Germany since 2010 has shown that the unique features of this new *Oxalis* plant are stable and reproduced true to type in successive generations.

SUMMARY OF THE INVENTION

Plants of the new *Oxalis* have not been observed under all possible environmental conditions. The phenotype may vary somewhat with variations in environment conditions such as temperature and light intensity without, however, any variance in genotype.

The following traits have been repeatedly observed and are determined to be the unique characteristics of 'Jroxachvel'. These characteristics in combination distinguish 'Jroxachvel' as a new and distinct *Oxalis* plant:

1. Upright, outwardly spreading and uniformly mounded plant habit.
2. Numerous basal leaves; dense and bushy plant form.

3. Freely flowering habit.
4. Dark brown-colored leaves.
5. White-colored flowers.
6. Relatively tolerant to high light levels.

Plants of the new *Oxalis* can be compared to plants of the female parent selection. Plants of the new *Oxalis* differ primarily from plants of the female parent selection in flowering time as plants of the new *Oxalis* flower for a longer period of time than plants of the female parent selection.

Plants of the new *Oxalis* can be compared to plants of the male parent selection. Plants of the new *Oxalis* differ primarily from plants of the male parent selection in leaf color as plants of the new *Oxalis* have more brownish-colored leaves than plants of the male parent selection during the autumn.

Plants of the new *Oxalis* can be compared to plants of *Oxalis regnellii* 'Jroxburwi', disclosed in U.S. Plant Pat. No. 17,557. Plants of the new *Oxalis* differ primarily from plants of 'Jroxburwi' in the following characteristics:

1. Plants of the new *Oxalis* are more vigorous than plants of 'Jroxburwi'.
2. Plants of the new *Oxalis* are more upright than plants of 'Jroxburwi'.
3. Plants of the new *Oxalis* flower for a longer period of time than plants of 'Jroxburwi'.
4. Plants of the new *Oxalis* and 'Jroxburwi' differ in leaf color as plants of 'Jroxburwi' have dark purple-colored leaves.

Plants of the new *Oxalis* can also be compared to plants of *Oxalis regnellii* 'Jroxfroja', disclosed in U.S. Plant Pat. No. 17,558. Plants of the new *Oxalis* differ primarily from plants of 'Jroxfroja' in the following characteristics:

1. Plants of the new *Oxalis* are more vigorous than plants of 'Jroxfroja'.
2. Plants of the new *Oxalis* are more upright than plants of 'Jroxfroja'.
3. Plants of the new *Oxalis* and 'Jroxfroja' differ in leaf color as plants of 'Jroxfroja' have dark green-colored leaves.

BRIEF DESCRIPTION OF THE PHOTOGRAPHS

The accompanying colored photographs illustrate the overall appearance of the new *Oxalis* plant showing the colors as true as it is reasonably possible to obtain in colored reproductions of this type. Colors in the photographs may differ slightly from the color values cited in the detailed botanical description which accurately describe the actual colors of the new *Oxalis* plant.

The photograph at the bottom of the sheet comprises a side perspective view of a typical flowering plant of 'Jroxachvel' grown in a container.

The photograph at the top of the sheet is a close-up view of a typical flowering plant of 'Jroxachvel'.

DETAILED BOTANICAL DESCRIPTION

The aforementioned photographs and following observations, measurements and values describe plants grown in one-gallon containers during the summer and early autumn in a polyethylene-covered greenhouse in Bonsall, Calif. under commercial production cultural practices. During the production of the plants, day temperatures ranged from 24° C. to 35° C. and night temperatures ranged from 14° C. to 20° C. Plants were nine weeks old when the photographs and description were taken. In the following description, color references are made to The Royal Horticultural Society Colour Chart, 2007 Edition, except where general terms of ordinary dictionary significance are used.

Botanical classification: *Oxalis regnellii* 'Jroxachvel'.

Parentage:

*Female, or seed, parent*.—Proprietary selection of *Oxalis regnellii* identified as code number M6, not patented.

*Male, or pollen, parent*.—Proprietary selection of *Oxalis regnellii* identified as code number L7, not patented.

Propagation:

*Type*.—By tissue culture.

*Time to initiate roots, summer*.—About seven days at 24° C.

*Time to initiate roots, winter*.—About ten days at 18° C.

*Time to produce a rooted young plant roots, summer*.—About six weeks at 24° C.

*Time to produce a rooted young plant, winter*.—About eight weeks at 18° C.

*Root description*.—Medium in thickness, fibrous; white in color.

*Rooting habit*.—Freely branching; medium density.

*Rhizome description*.—Quantity per container: About 40 rhizomes develop per container. Length: About 1.7 cm. Diameter: About 8 mm. Scale length: About 7 mm. Scale width: About 5 mm. Texture: Smooth, glabrous. Color: Close to N171C to N171D.

Plant description:

*Plant form/growth habit*.—Herbaceous perennial flowering plant; upright, outwardly spreading and uniformly mounded plant habit; vigorous growth habit.

*Plant height*.—About 20 cm.

*Plant diameter*.—About 35 cm.

Foliage description:

*Arrangement*.—Leaves basal, clumping and arising from rhizomes; leaves clover-like, palmate three-foliate.

*Leaflet length*.—About 3 cm.

*Leaflet width*.—About 5 cm.

*Leaflet shape*.—Broadly triangular.

*Leaflet apex*.—Emarginate.

*Base*.—Attenuate.

*Margin*.—Entire.

*Texture, upper and lower surfaces*.—Smooth, glabrous.

*Venation pattern*.—Pinnate; reticulate.

*Color*.—Developing leaves, upper surface: Close to 200B. Developing leaves, lower surface: Close to 187B. Fully expanded leaves, upper surface: Close to 200A; venation, close to 200A. Fully expanded leaves, lower surface: Close to 187B; venation, close to 187B.

*Petiole*.—Length: About 20.8 cm. Diameter: About 2 mm. Texture, upper and lower surfaces: Smooth, glabrous. Color, upper and lower surfaces: Close to 147C to 147D.

Flower description:

*Flower type and habit*.—Rotate single flowers arranged in loose umbels; flowers facing upright or outwardly and positioned just above the foliar plane; freely flowering habit, about five to six flowers per umbel.

*Fragrance*.—None detected.

*Natural flowering season*.—Plants of the new *Oxalis* flower continuously year-round in Southern California.

*Time to flower*.—Early flowering habit, plants begin flowering about four to five weeks after planting.

*Flower longevity on the plant*.—About three to four days; flowers not persistent.

*Inflorescence height*.—About 3 cm to 3.5 cm.

*Inflorescence diameter*.—About 4 cm.

*Flower diameter*.—About 1.8 cm.

*Flower depth*.—About 1 cm.

*Flower buds*.—Length: About 1.3 cm. Diameter: About 3 mm. Shape: Elongated oblong. Color: Close to NN155B.

*Petals*.—Quantity/arrangement: Five petals arranged in a single whorl. Length: About 2 cm. Width: About 6 mm. Shape: Obovate. Apex: Rounded. Base: Attenuate. Margin: Entire. Texture, upper and lower surfaces: Smooth, glabrous; satiny. Color: When opening, upper surface: Close to NN155D. When opening, lower surface: Close to NN155C. Fully opened, upper and lower surfaces: Close to NN155D; towards the base, close to 145B.

*Sepals*.—Quantity/arrangement: Five sepals arranged in a single whorl. Length: About 6 mm. Width: About 2 mm. Shape: Lanceolate. Apex: Acute. Base: Fused. Margin: Entire. Texture, upper and lower surfaces: Smooth, glabrous. Color, upper surface: Close to 145B. Color, lower surface: Close to 145A.

*Peduncles*.—Length: About 21 cm. Width: About 2 mm. Strength: Strong. Angle: Upright to outwardly. Texture: Smooth, glabrous. Color: Close to 145A.

*Pedicels*.—Length: About 1.5 cm. Width: About 1 mm. Strength: Moderately strong. Angle: About 30° to 45° from peduncle axis. Texture: Smooth, glabrous. Color: Close to 145A.

*Reproductive organs*.—Stamens: Quantity: About ten in two whorls. Filament length: About 4 mm. Filament color: Close to 157D. Anther shape: Oval. Anther length: Less than 1 mm. Anther color: Close to 3D. Pollen amount: Scarce. Pollen color: Close to 3C. Pistils: Quantity: One per flower. Pistil length: About 5 mm. Stigma shape: Round. Stigma color: Close to 144A. Style length: About 2 mm. Style color: Close to 144B. Ovary color: Close to 145B.

*Seed/fruit*.—Seed and fruit production have not been observed.

Disease/pest resistance: Plants of the new *Oxalis* have not been noted to be resistant to pathogens and pests common to *Oxalis*.

Temperature tolerance: Plants of the new *Oxalis* have been observed to tolerate temperatures from about 5° C. to about 40° C.

High light tolerance: Plants of the new *Oxalis* have been observed to be relatively tolerant to high light levels.

It is claimed:

1. A new and distinct *Oxalis* plant named 'Jroxachvel' as illustrated and described.

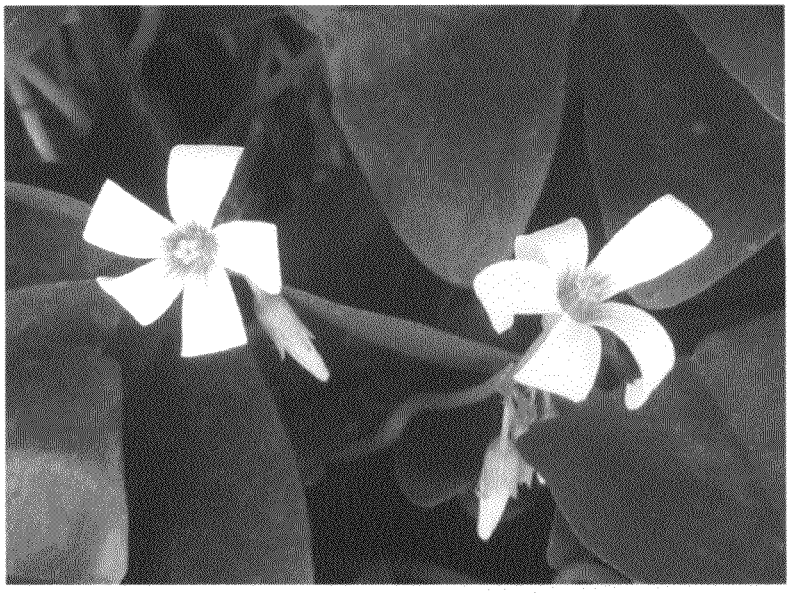
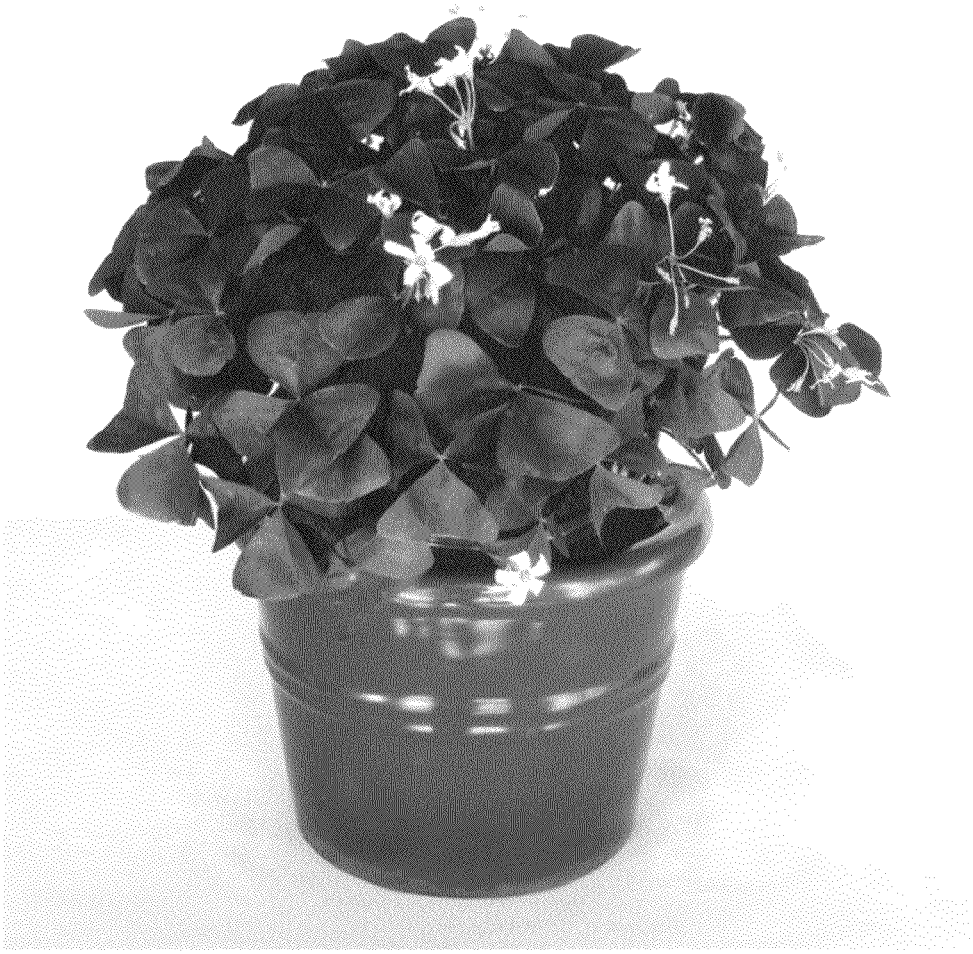

* * * * *